United States Patent
Rafferty et al.

(10) Patent No.: US 6,323,243 B1
(45) Date of Patent: Nov. 27, 2001

(54) TYROSINE-DERIVED COMPOUNDS AS CALCIUM CHANNEL ANTAGONISTS

(75) Inventors: Michael Francis Rafferty; Yuntao Song, both of Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/694,921

(22) Filed: Oct. 24, 2000

Related U.S. Application Data

(62) Division of application No. 09/381,938, filed as application No.PCT/US99/12274 on Jun. 2, 1999, now Pat. No. 6,180,677.
(60) Provisional application No. 60/094,704, filed on Jul. 30, 1998.

(51) Int. Cl.[7] .................. A61K 31/132; A61K 31/135; C07C 211/42
(52) U.S. Cl. .................. 514/741; 514/724; 514/727; 514/730; 564/306; 564/336; 564/430
(58) Field of Search .................. 564/306, 336, 564/430; 514/740, 741, 724, 727, 730

(56) References Cited

FOREIGN PATENT DOCUMENTS

| 0 159 396 | 10/1985 | (EP) . |
|---|---|---|
| 0 805 147 | 11/1997 | (EP) . |
| 94/24116 | 10/1994 | (WO) . |
| 98/54123 | 12/1998 | (WO) . |

OTHER PUBLICATIONS

Caplus 83:10895 English abstract DE 2446005 RN #52553–01–2 , Mar. 4, 1975.*
Caplus 128:172126 English Abstract US 5952294 RN #14500–78–8. May 2, 1998.*
Chem Abstract 1999: 110284, Lazo John, et al., RN: 145400–78–8.
Chem Abstract 2000: 50574 Sullivan G, et al. RN#256653–23–3, 256654–09–5.
Chem Abstract 76: 42807, Fujino Masahiko, et al., RN #52553–01–2.

* cited by examiner

Primary Examiner—Alan L. Rotman
Assistant Examiner—Rita Desai
(74) Attorney, Agent, or Firm—Charles W. Ashbrook; David R. Kurlandsky

(57) ABSTRACT

The present invention provides compounds that block calcium channels and have the Formula I:

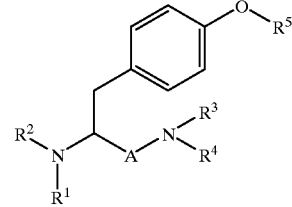

and pharmaceutically acceptable salts, esters, and pro-drugs thereof, wherein $R^1$ and $R^2$ are independently H, phenylcyclopentylcarbonyl, $C_1$–$C_7$ alkyl, cyclohexylmethyl, benzyl, $C_1$–$C_5$ alkylbenzyl, or $C_1$–$C_5$ alkoxybenzyl, A is —C(O)— or —$CH_2$—;

$R^3$ is H or —$CH_3$;

$R^4$ is $C_1$–$C_4$ alkyl or piperidin-1-ylethyl;

$R^5$ is phenyl-$(CH_2)_n$—, $C_1$–$C_4$ alkylphenyl-$(CH_2)_n$—, or halophenyl-$(CH_2)_n$—; and n is 1 or 2.

The present invention also provides pharmaceutical compositions containing the compounds of Formula I and methods of using them to treat stroke, cerebral ischemia, head trauma, and epilepsy.

18 Claims, No Drawings

TYROSINE-DERIVED COMPOUNDS AS CALCIUM CHANNEL ANTAGONISTS

This application is a divisional application of U.S. Ser. No. 09/381,938 filed Sep. 27, 1999, now U.S. Pat. No. 6,180,677, which is a 371 of Application No. PCT/US99/12274 filed Jun. 2, 1999, which claims benefit of Provisional Application U.S. Ser. No. 60/094,704 filed Jul. 30, 1998.

BACKGROUND OF THE INVENTION

1. Field of the Invention

The present invention relates to compounds that act to block calcium channels; methods of using the compounds to treat stroke, cerebral ischemia, pain, head trauma, or epilepsy; and to pharmaceutical compositions that contain the compounds of the present invention.

2. Summary of the Related Art

The entry of excessive amounts of calcium ions into neurons following an ischemic episode or other neuronal trauma has been well documented. Uncontrolled high concentrations of calcium in neurons initiate a cascade of biochemical events that disrupts normal cellular processes. Among these events are the activation of proteases and lipases, the breakdown of neuronal membranes, and the formation of free radicals, which may ultimately lead to cell death. Several types of calcium channels, the L, N, P, Q, R, and T types, have been discovered. Each type possesses distinct structural features, functional properties and cellular/subcellular distributions. Type-selective calcium channel blockers also have been identified. For example, SNX-111 has been shown to be a selective N-type calcium channel blocker and has demonstrated activity in a number of models of ischemia and pain (Bowersox S. S., et al., *Drug News and Perspective,* 1994:7:261–268 and references cited therein). The compounds of the present invention are calcium channel blockers that can block N-type calcium channels and can be used to treat stroke, pain, cerebral ischemia, head trauma, and epilepsy.

SUMMARY OF THE INVENTION

The present invention provides compounds that block calcium channels and have the Formula I:

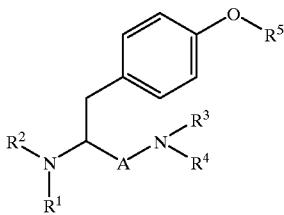

I and pharmaceutically acceptable salts, esters, and pro-drugs thereof, wherein $R^1$–$R^5$ are defined below.

The present invention also provides pharmaceutical compositions containing the compounds of Formula I and methods of using them to treat stroke, cerebral ischemia, head trauma, and epilepsy.

DETAILED DESCRIPTION OF THE INVENTION

The present invention comprises novel calcium channel blockers having general structural Formula I:

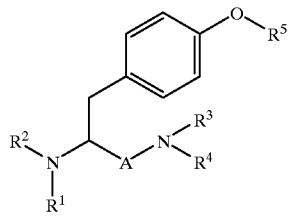

I and pharmaceutically acceptable salts, esters, and pro-drugs thereof, wherein $R^1$ and $R^2$ are independently H, phenylcyclopentylcarbonyl, $C_1$–$C_7$ alkyl, cyclohexylmethyl, benzyl, $C_1$–$C_5$ alkylbenzyl, or $C_1$–$C_5$ alkoxybenzyl;

A is —C(O)— or —$CH_2$—;

$R^3$ is H or —$CH_3$;

$R^4$ is $C_1$–$C_4$ alkyl or piperidin-1-ylethyl;

$R^5$ is phenyl-$(CH_2)_n$—, $C_1$–$C_4$ alkylphenyl-$(CH_2)_n$—, or halophenyl-$(CH_2)_n$—; and n is 1 or 2.

The term "alkyl" means a straight or branched chain hydrocarbon. Representative examples of alkyl groups are methyl, ethyl, propyl, isopropyl, isobutyl, butyl, tert-butyl, sec-butyl, pentyl, hexyl, $(CH_3)_2CHCH_2CH_2$—, $((CH_3)_2CHCH_2CH_2)_2CH$—, and $(CH_3)_3CCH_2CH_2$.

The term "alkoxy" means an alkyl group attached to an oxygen atom. Representative examples of alkoxy groups include methoxy, ethoxy, tert-butoxy, propoxy, and isobutoxy.

The term "halo" means chlorine, fluorine, bromine, and iodine.

The symbol "-" means a bond.

Most preferably, the invention provides compounds of Formula I selected from the group consisting of:

(S)-1-Phenyl-cyclopentanecarboxylic acid [2-(4-benzyloxy-phenyl)-1-tert-butylcar-bamoyl-ethyl]-amide;

(S)-3-(4-Benzyloxy-phenyl)-N-tert-butyl-2-(3-methyl-butylamino)-propionamide;

(S)-3-(4-Benzyloxy-phenyl)-2-[bis-(3-methyl-butyl)-amino]-N-tert-butyl-propion-amide;

(S)-3-(4-Benzyloxy-phenyl)-N-tert-butyl-2-[4-methyl-1-(3-methyl-butyl)-pentyl-amino]-propionamide;

(S)-3-(4-Benzyloxy-phenyl)-N-tert-butyl-2-[cyclohexyl-methyl-(3-methyl-butyl)-amino]-propionamide;

(S)-3-(4-Benzyloxy-phenyl)-N-tert-butyl-2-[(3,3-dimethyl-butyl)-(3-methyl-butyl)-amino]-propionamide;

(S)-3-(4-Benzyloxy-phenyl)-N-tert-butyl-2-(3,3-dimethyl-butylamino)-propionamide;

(S)-3-(4-Benzyloxy-phenyl)-2-[bis-(3,3-dimethyl-butyl)-amino]-N-tert-butyl-propion-amide;

(S)-3-(4-Benzyloxy-phenyl)-N-tert-butyl-2-(4-tert-butyl-benzylamino)-propionamide;

(S)-3-(4-Benzyloxy-phenyl)-2-[bis-(4-tert-butyl-benzyl)-amino]-N-(2-piperidin-1-yl-ethyl)-propionamide;

3-(4-Benzyloxy-phenyl)-$N^2$,$N^2$-bis-(4-tert-butyl-benzyl)-$N^1$-(2-piperidin-1-yl-ethyl)-propane-1,2-diamine;

3-(4-Benzyloxy-phenyl)-$N^2$-(4-tert-butyl-benzyl)-$N^1$-(2-piperidin-1-yl-ethyl)-propane-1,2-diamine;

(S)-3-(4-Benzyloxy-phenyl)-2-(4-tert-butyl-benzylamino)-N-(2-piperidin-1-yl-ethyl)-propionamide; and 3-(4-Benzyloxy-phenyl)-$N^1$-tert-butyl-$N^2$-(4-tert-butyl-benzyl)-propane-1,2-diamine.

The term "patient" means all animals including humans. Examples of patients include humans, cows, dogs, cats, goats, sheep, and pigs.

The compounds of the invention may be readily prepared as set forth in the following reaction schemes which employ common synthetic methods well-known to those skilled in organic chemistry. The following terms are as defined:

| | |
|---|---|
| HBTU | O-benzotriazol-1-yl-N,N,N',N'-tetramethyluronium-hexafluorophosphate |
| TFA | Trifluoroacetic acid |
| DMC | 4,4'-Dichloro-α-methylbenzhydrol |
| DMF | N,N-Dimethylformamide |
| LAH | Lithium aluminum hydride |
| THF | Tetrahydrofuran |
| NaHB(Oac)$_3$ | Sodium triacetoxyborohydride |
| Et$_2$O | Diethyl ether |

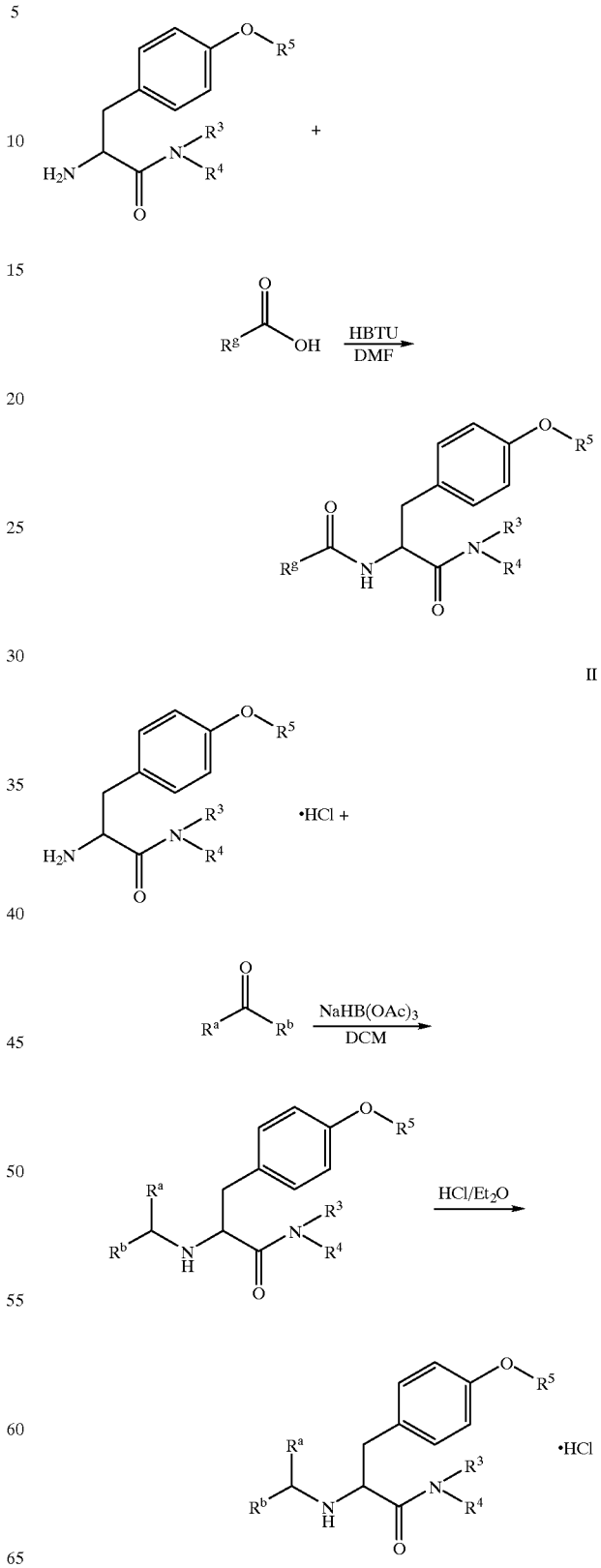

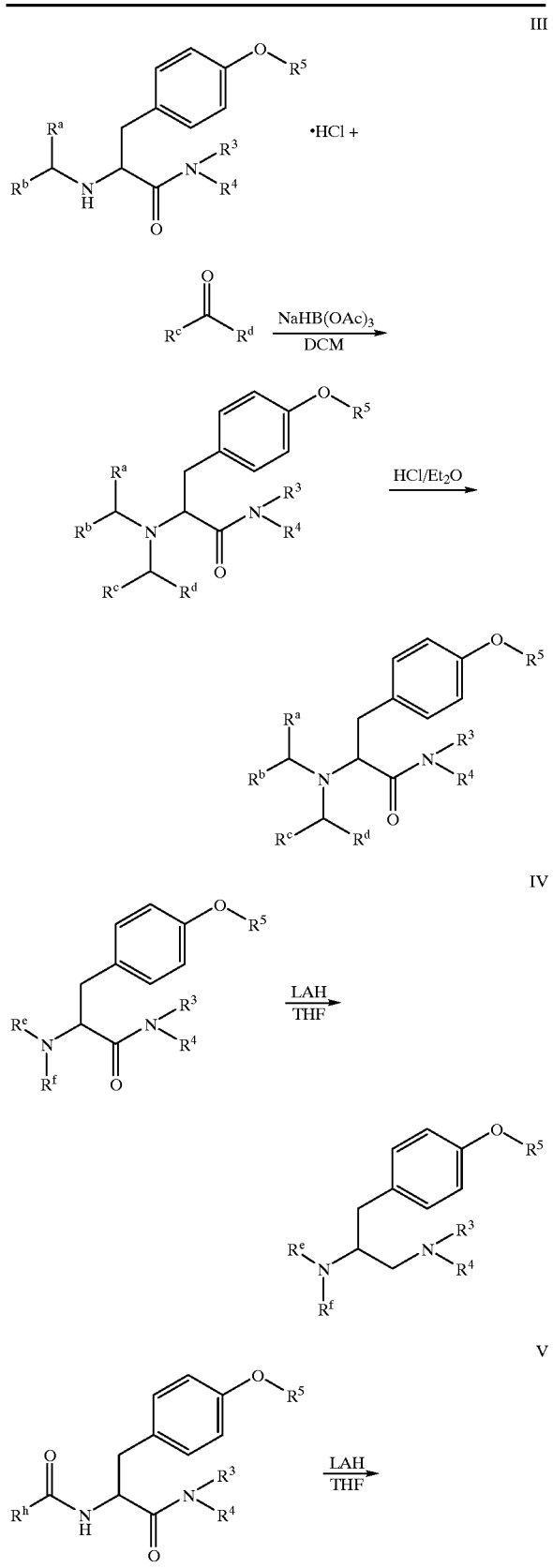

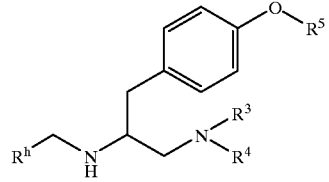

Each of $R^a$–$R^h$ are defined to encompass all chemical moieties for which the reaction products of Schemes I through IV fall within the scope of Formula I.

Those skilled in the art are easily able to identify patients having a stroke or at risk of having a stroke, cerebral ischemia, head trauma, or epilepsy. For example, patients who are at risk of having a stroke include, but are not limited to, patients having hypertension or undergoing major surgery.

A therapeutically effective amount is an amount of a compound of Formula I that when administered to a patient, ameliorates a symptom of the disease. Typical amounts will be about 0.01 to about 200 mg/kg of body weight. Daily dose will generally be from about 5 to about 500 mg per patient.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers (for example, ethyl alcohol, isopropyl alcohol, ethyl carbonate, ethyl acetate, benzyl alcohol, benzyl benzoate, propyleneglycol, 1,3-butyleneglycol, dimethylformamide), oils (in particular, cottonseed oil, groundnut oil, corn germ oil, olive oil, castor oil, and sesame oil), glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening agents, flavoring agents, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or intravaginal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature, and therefore melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use. The term also includes the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to, ammonium, tetramethylammonium, tetraethylammonium, methylamine, dimethylamine, trimethylamine, ethylamine, triethylamine, and the like. (See, for example, S. M. Berge, et al., "Pharmaceutical Salts," *J. Pharm. Sci.*, 1977;66:1–19, which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to, benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines, wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kg, a dosage in the range of about 0.01 to about 100 mg/kg of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

EXAMPLE 1

(S)-1-Phenyl-cyclopentanecarboxylic acid [2-(4-benzyloxy-phenyl)-1-tert-butylcarbamoyl-ethyl]-amide

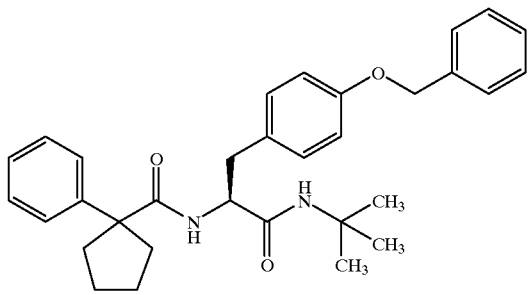

Step A (S)-[2-[(1,1-dimethylethyl)amino]-2-oxo-1-(phenylmethyl)ethyl]-carbamic acid 1,1-dimethylethyl ester

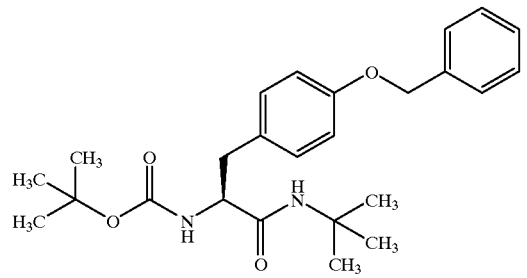

A solution of N-(tert-Butyloxycarbonyl)-O-benzyl-L-tyrosine (Bachem, 2.00 g, 5.38 mmol) in 20 mL of DMF was cooled to 0° C. and treated with i-Pr$_2$NEt (1.5 mL, Aldrich, Milwaukee, Wis.) followed by O-benzotriazol-1-yl-N,N,N',N'-tetramethyluronium hexafluoro-phosphate (2.04 g, 5.38 mmol, Novabiochem, La Jolla, Calif.). The resulting suspension was stirred for 30 minutes at 0° C. and then treated with tert-butylamine (0.48 g, 6.56 mmol, Aldrich, Milwaukee, Wis.). The reaction mixture was stirred for 1 hour at 0° C. and warmed to room temperature. The reaction mixture was then poured into Et$_2$O, and washed sequentially with saturated aqueous NaHCO$_3$ solution and saturated aqueous NaCl solution. The organic phase was dried over MgSO$_4$, filtered, and concentrated. The crude residue was purified by chromatography (silica gel, 3:1 heptane/ethyl acetate) to give (S)-[2-[(1,1-dimethylethyl)amino]-2-oxo-1-(phenylmethyl)ethyl]-carbamic acid 1,1-dimethylethyl ester (2.65 g).

MS (CI) 427 (MH)$^+$.

Step B (S)-2-Amino-3-(4-benzyloxy-phenyl)-N-tert-butyl-propionamide

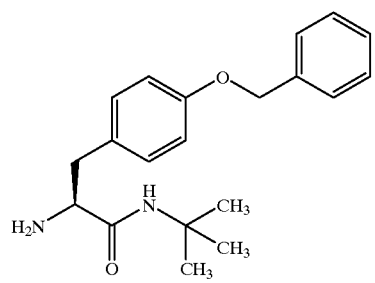

A solution of (S)-[2-(4-benzyloxy-phenyl)-1-tert-butylcarbamoyl-ethyl]-carbamic acid tert-butyl ester (6.0 g, 14.1 mmol, Example 1, Step A) in CH$_2$Cl$_2$ (28 mL) was treated with trifluoroacetic acid (28 mL). The resulting solution was stirred for 20 minutes and then concentrated. The residue was diluted with EtOAc (300 mL), washed with saturated bicarbonate solution (2×300 mL) and brine (300 mL), dried over Na$_2$SO$_4$, and concentrated to give 4.2 g (91%) of (S)-2-Amino-3-(4-benzyloxy-phenyl)-N-tert-butyl-propionamide.

MS: 328 (M$^{+1}$ for C$_{20}$H$_{26}$N$_2$O$_3$).

TLC: Silica gel, R$_f$ 0.43 (10% MeOH/CH$_2$Cl$_2$).

Step C

1-Phenyl-1-cyclopentanecarboxylic acid (0.171 g, 0.899 mmol) was dissolved in dry DMF (3 mL) under a nitrogen atmosphere and cooled to 0° C. in an ice-water bath. To this solution were added in succession N,N-diisopropylethylamine (0.310 mL, 1.80 mmol) and solid O-benzotriazol-1-yl-N,N,N',N'-tetramethyluronium hexafluorophosphate (0.341 g, 0.899 mmol, Novabiochem, La Jolla, Calif.). The resulting reaction mixture was stirred at 0° C. for 30 minutes, (S)-2-Amino-3-(4-benzyloxy-phenyl)-N-tert-butyl-propionamide (0.293 g, 0.899 mmol) was then added. After an additional 60 minutes stirring at 0° C., the reaction mixture was mixed with 60 mL of diethyl ether. The resulting mixture was successively washed with 5% aqueous HCl solution, brine, saturated aqueous NaHCO$_3$ solution and brine, and was dried over Na$_2$SO$_4$. The solution was concentrated in vacuo, and an oil was obtained. The crude residue was purified by chromatography (silica gel, 60% ether in hexanes) to give the title compound as a white foam (0.20 g, 45%); mp 40–50° C.

APCI-MS: m/z 499.6 (MH$^+$).

EXAMPLE 2

(S)-3-(4-Benzyloxy-phenyl)-N-tert-butyl-2-(3-methyl-butylamino)-propionamide monohydrochloride

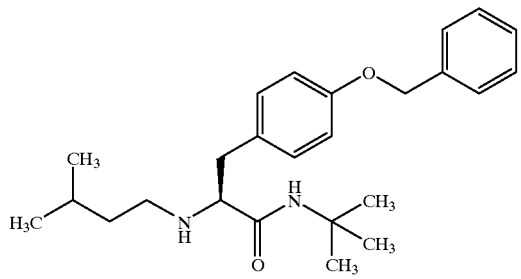

Step A (S)-2-Amino-3-(4-benzyloxy-phenyl)-N-tert-butyl-propionamide monohydrochloride

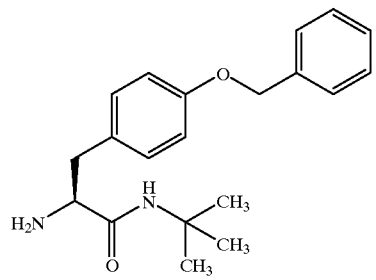

To a solution of (S)-2-amino-3-(4-benzyloxy-phenyl)-N-tert-butyl-propionamide (Example 1, Step B) in ether was added excess amount of ethereal HCl. The solid formed was isolated via filtration, and subsequent drying under vacuum gave (S)-2-Amino-3-(4-benzyloxy-phenyl)-N-tert-butyl-propionamide monohydrochloride as a yellow solid.

Step B (S)-2-amino-3- (4-benzyloxy-phenyl)-N-tert-butyl-propionamide monohydrochloride (5.0 g, 14 mmol, Example 2, Step A) and isovaleraldehyde (1.5 mL, 14 mmol, Aldrich, Milwaukee, Wis.) were mixed in $CH_2Cl_2$ (70 mL). After stirring at ambient temperature under a nitrogen atmosphere for 30 minutes, the solution was cooled to 0° C. in an ice-water bath. To this solution was added sodium triacetoxyborohydride (4.4 g, 21 mmol). The resulting reaction mixture was stirred for 30 minutes at 0° C., followed by an additional 12 hours at ambient temperature. Saturated aqueous $NaHCO_3$ solution (100 mL) was added to the reaction mixture, and the resulting mixture was stirred for 5 minutes. The two layers were separated and the aqueous layer was extracted with $CH_2Cl_2$ (2×70 mL). The combined organic solution was dried over $Na_2SO_4$. TLC (70% EtOAc in Hexanes as the eluant) showed two spots with $R_f$ values of 0.84 and 0.51. The solution was concentrated in vacuo affording a viscous oil. The lower spot on the TLC ($R_f$=0.51) was isolated by flash chromatography (50% EtOAc in hexanes). The free amine was dissolved in 20 mL of ethyl ether and treated with ethereal HCl to afford 3.67 g (62%) of the pure titled compound as a white solid; mp 182–184° C.

APCI-MS: m/z 397.9 (MH$^+$).

EXAMPLE 3

(S)-3-(4-Benzyloxy-phenyl)-2-[bis-(3-methyl-butyl)-amino]-N-tert-butyl-propionamide monohydrochloride

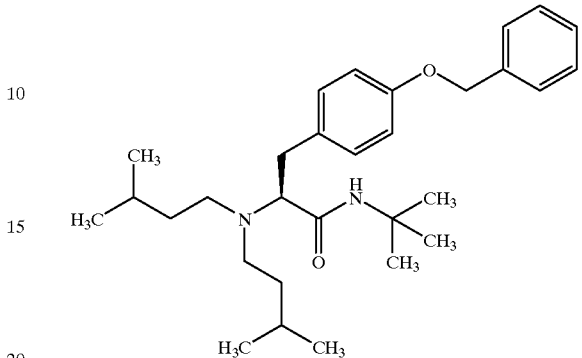

(S)-2-Amino-3-(4-benzyloxy-phenyl)-N-tert-butyl-propionamide monohydrochloride (5.0 g, 14 mmol, Example 2, Step A) and isovaleraldehyde (1.5 mL, 14 mmol, Aldrich, Milwaukee, Wis.) were mixed in $CH_2Cl_2$ (70 mL). After stirring at ambient temperature under a nitrogen atmosphere for 30 minutes, the solution was cooled to 0° C. in an ice-water bath. To this solution was added sodium triacetoxyborohydride (4.4 g, 21 mmol). The resulting reaction mixture was stirred for 30 minutes at 0° C., followed by an additional 12 hours at ambient temperature. Saturated aqueous $NaHCO_3$ solution (100 mL) was added to the reaction mixture, and the resulting mixture was stirred for 5 minutes. The two layers were separated, and the aqueous layer was extracted with $CH_2Cl_2$ (2×70 mL). The combined organic solution was dried over $Na_2SO_4$. TLC (70% EtOAc in Hexanes as the eluant) showed two spots with $R_f$ values of 0.84 and 0.51. The solution was concentrated in vacuo affording a viscous oil. The higher spot on the TLC ($R_f$= 0.84) was isolated by flash chromatography (50% EtOAc in hexanes). The free amine was dissolved in 10 mL of ethyl ether and treated with ethereal HCl to afford 0.70 g (10%) of the pure titled compound as a white solid; mp 50–60° C.

APCI-MS: m/z 467.7 (MH$^+$).

EXAMPLE 4

(S)-3-(4-Benzyloxy-phenyl)-N-tert-butyl-2-[4-methyl-1-(3-methyl-butyl)-pentylamino]-propionamide monohydrochloride

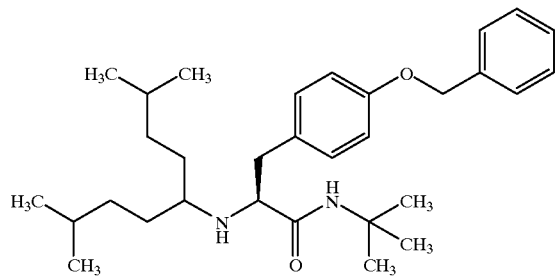

(S)-2-Amino-3-(4-benzyloxy-phenyl)-N-tert-butyl-propionamide monohydrochloride (1.04 g, 2.87 mmol, Example 2, Step A) and diisoamyl ketone (0.490 g, 2.87 mmol, Aldrich, Milwaukee, Wis.) were mixed in CH₂Cl₂ (25 mL). After stirring at ambient temperature under a nitrogen atmosphere for 30 minutes, the solution was cooled to 0° C. in an ice-water bath. To this solution was added sodium triacetoxyborohydride (0.910 g, 4.30 mmol). The resulting reaction mixture was stirred for 30 minutes at 0° C., followed by an additional 12 hours at ambient temperature. Saturated aqueous NaHCO₃ solution (25 mL) was added to the reaction mixture, and the resulting mixture was stirred for 5 minutes. The two layers were separated, and the aqueous layer was extracted with CH₂Cl₂ (2×30 mL). The combined organic solution was dried over Na₂SO₄. The solution was concentrated in vacuo affording a viscous oil. The crude product was further purified by flash chromatography (25% EtOAc in hexanes). The free amine was dissolved in 10 mL of ethyl ether and treated with ethereal HCl to afford 0.45 g (30%) of the pure titled compound as a white solid; mp 114–115° C.

APCI-MS: m/z 481.3 (MH⁺).

EXAMPLE 5

(S)-3-(4-Benzyloxy-phenyl)-N-tert-butyl-2-[cyclohexyl-methyl-(3-methyl-butyl)-amino]-propionainide monohydrochloride

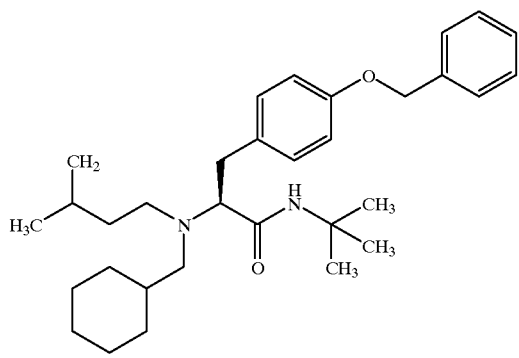

(S)-3-(4-Benzyloxy-phenyl)-N-tert-butyl-2-(3-methyl-butylamino)-propionamide monohydrochloride (1.0 g, 2.3 mmol, Example 2) and cyclohexanecaboxaldehyde (0.28 g, 2.3 mmol, Aldrich, Milwaukee, Wis.) were mixed in CH₂Cl₂ (25 mL). After stirring at ambient temperature under a nitrogen atmosphere for 30 minutes, the solution was cooled to 0° C. in an ice-water bath. To this solution was added sodium triacetoxyborohydride (0.73 g, 3.4 mmol). The resulting reaction mixture was stirred for 30 minutes at 0° C., followed by an additional 12 hours at ambient temperature. Saturated aqueous NaHCO₃ solution (25 mL) was added to the reaction mixture, and the resulting mixture was stirred for 5 minutes. The two layers were separated, and the aqueous layer was extracted with CH₂Cl₂ (2×30 mL). The combined organic solution was dried over Na₂SO₄. The solution was concentrated in vacuo affording a viscous oil. The crude product was further purified by flash chromatography (20% EtOAc in hexanes). The free amine was dissolved in 10 mL of ethyl ether and treated with ethereal HCl to afford 0.70 g (58%) of the pure titled compound as a white foam; mp 70–81° C.

APCI-MS: m/z 493.3 (MH⁺).

EXAMPLE 6

(S)-3-(4-Benzyloxy-phenyl)-N-tert-butyl-2-[(3,3-dimethyl-butyl)-(3-methyl-butyl)-amino]-propionamide monohydrochloride

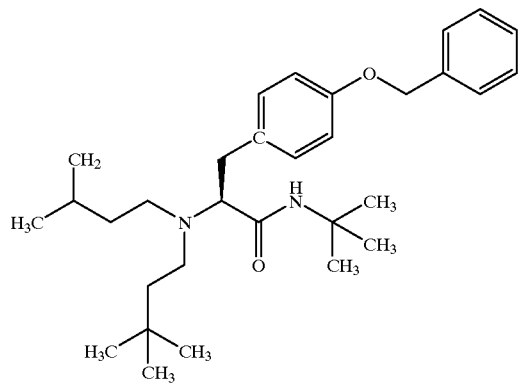

(S)-3-(4-Benzyloxy-phenyl)-N-tert-butyl-2-(3-methyl-butylamino)-propionamide mono-hydrochloride (0.78 g, 1.8 mmol, Example 2) and 3,3-dimethylbutyraldehyde (0.18 g, 1.8 mmol, Aldrich, Milwaukee, Wis.) were mixed in CH₂Cl₂ (19 mL). After stirring at ambient temperature under a nitrogen atmosphere for 30 minutes, the solution was cooled to 0° C. in an ice-water bath. To this solution was added sodium triacetoxyborohydride (0.60 g, 2.7 mmol). The resulting reaction mixture was stirred for 30 minutes at 0° C., followed by an additional 12 hours at ambient temperature. Saturated aqueous NaHCO₃ solution (20 mL) was added to the reaction mixture, and the resulting mixture was stirred for 5 minutes. The two layers were separated, and the aqueous layer was extracted with CH₂Cl₂ (2×20 mL). The combined organic solution was dried over Na₂SO₄. The solution was concentrated in vacuo affording a viscous oil. The crude product was further purified by flash chromatography (20% EtOAc in hexanes). The free amine was dissolved in 10 mL of ethyl ether and treated with ethereal HCl to afford 0.62 g (67%) of the pure titled compound as a white foam; mp 65–72° C.

APCI-MS: m/z 481.3 (MH⁺).

EXAMPLE 7

(S)-3-(4-Benzyloxy-phenyl)-N-tert-butyl-2-(3,3-dimethyl-butylamino)-propionamide monohydrochloride

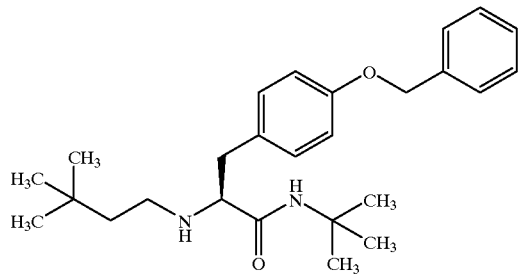

(S)-2-Amino-3-(4-benzyloxy-phenyl)-N-tert-butyl-propionamide monohydrochloride (1.74 g, 4.80 mmol, Example 2, Step A) and 3,3-dimethylbutyraldehyde (0.48 g, 4.8 mmol, Aldrich, Milwaukee, Wis.) were mixed in CH$_2$Cl$_2$ (24 mL). After stirring at ambient temperature under a nitrogen atmosphere for 30 minutes, the solution was cooled to 0° C. in an ice-water bath. To this solution was added sodium triacetoxyborohydride (1.53 g, 7.20 mmol). The resulting reaction mixture was stirred for 30 minutes at 0° C., followed by an additional 12 hours at ambient temperature. Saturated aqueous NaHCO$_3$ solution (24 mL) was added to the reaction mixture, and the resulting mixture was stirred for 5 minutes. The two layers were separated, and the aqueous layer was extracted with CH$_2$Cl$_2$ (2×25 mL). The combined organic solution was dried over Na$_2$SO$_4$. TLC (50% EtOAc in Hexanes as the eluant) showed two spots with R$_f$ values 0.87 and 0.39. The solution was concentrated in vacuo affording a viscous oil. The lower spot on the TLC (R$_f$=0.39) was isolated by flash chromatography (40% EtOAc in hexanes). The free amine was dissolved in 20 mL of ethyl ether and treated with ethereal HCl to afford 1.29 g (60%) of the pure titled compound as a white solid; mp 238–240° C.

APCI-MS: m/z 411.1 (MH$^+$).

EXAMPLE 8

(S)-3-(4-Benzyloxy-phenyl)-2-[bis-(3,3-dimethyl-butyl)-amino]-N-tert-butyl-propionamide monohydrochloride

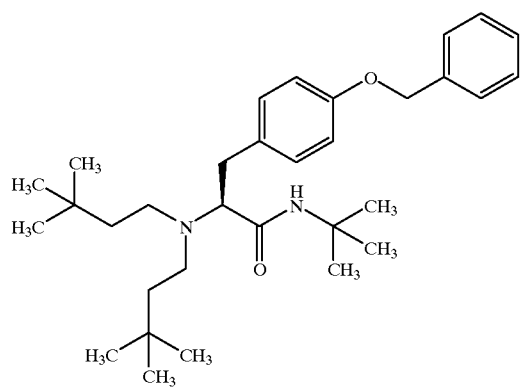

S)-2-Amino-3-(4-benzyloxy-phenyl)-N-tert-butyl-propionamide monohydrochloride (1.74 g, 4.80 mmol, Example 2, Step A) and 3,3-dimethylbutyraldehyde (0.48 g, 4.8 mmol, Aldrich, Milwaukee, Wis.) were mixed in CH$_2$Cl$_2$ (24 mnL). After stirring at ambient temperature under a nitrogen atmosphere for 30 minutes, the solution was cooled to 0° C. in an ice-water bath. To this solution was added sodium triacetoxyborohydride (1.53 g, 7.20 mmol). The resulting reaction mixture was stirred for 30 minutes at 0° C., followed by an additional 12 hours at ambient temperature. Saturated aqueous NaHCO$_3$ solution (24 mL) was added to the reaction mixture, and the resulting mixture was stirred for 5 minutes. The two layers were separated, and the aqueous layer was extracted with CH$_2$Cl$_2$ (2×25 mL). The combined organic solution was dried over Na$_2$SO$_4$. TLC (50% EtOAc in Hexanes as the eluant) showed two spots with R$_f$ values 0.87 and 0.39. The solution was concentrated in vacuo affording a viscous oil. The higher spot on the TLC (R$_f$=0.87) was isolated by flash chromatography (40% EtOAc in hexanes). The free amine was dissolved in 20 mL of ethyl ether and treated with ethereal HCl to afford 0.33 g (13%) of the pure titled compound as a white foam; mp 75–85° C.

APCI-MS: m/z 495.1 (MH$^+$).

EXAMPLE 9

(S)-3-(4-Benzyloxy-phenyl)-N-tert-butyl-2-(4-tert-butyl-benzylamino)-propionamide monohydrochloride

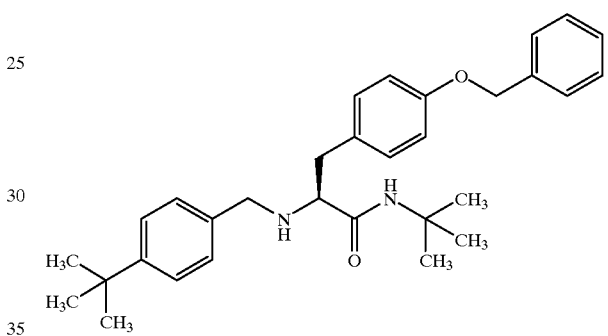

(S)-2-Amino-3-(4-benzyloxy-phenyl)-N-tert-butyl-propionamide monohydrochloride (3.85 g, 10.6 mmol, Example 2, Step A) and 4-tert-butylbenzaldehyde (1.72 g, 10.6 mmol, Aldrich, Milwaukee, Wis.) were mixed in CH$_2$Cl$_2$ (54 mL). After stirring at ambient temperature under a nitrogen atmosphere for 30 minutes, the solution was cooled to 0° C. in an ice-water bath. To this solution was added sodium triacetoxyborohydride (3.37 g, 15.9 mmol). The resulting reaction mixture was stirred for 30 minutes at 0° C., followed by an additional 12 hours at ambient temperature. Saturated aqueous NaHCO$_3$ solution (77 mL) was added to the reaction mixture, and the resulting mixture was stirred for 5 minutes. The two layers were separated, and the aqueous layer was extracted with CH$_2$Cl$_2$ (2×70 mL). The combined organic solution was dried over Na$_2$SO$_4$. The solution was concentrated in vacuo affording a viscous oil. Title compound was isolated by flash chromatography (30% EtOAc in hexanes). The free amine was dissolved in 20 mL of ethyl ether and treated with ethereal HCl to afford 1.71 g (34%) of the pure titled compound as a white foam; mp 95–105° C.

APCI-MS: m/z 473.0 (MH$^+$).

EXAMPLE 10

(S)-3-(4-Benzyloxy-phenyl)-2-[bis-(4-tert-butyl-benzyl)-amino]-N-(2-piperidin-1-yl-ethyl)-propionamide

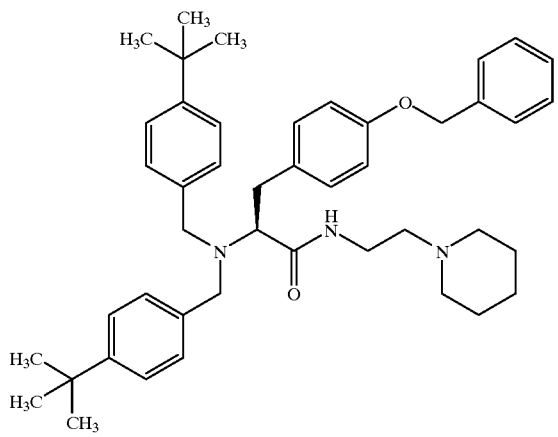

Step A (S)-[2-(4-Benzyloxy-phenyl)-1-(2-piperidin-1-yl-ethylcarbamoyl)-ethyl]-carbamic acid tert-butyl ester

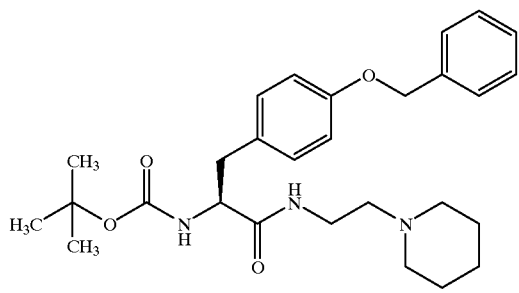

A solution of 27.9 g (75 mmol) 3-(4-benzyloxy-phenyl)-2-tert-butoxycarbonylamino-propionic acid, (Bachem Inc., Torrance, Calif. 90505) 16.5 mL (150 mmol) 4-methylmorpholine, and 28.5 g (75 mmol) O-Benzotriazol-1-yl-N,N,N',N'-bis(tetramethylene)uronium hexafluorophosphate in 110 mL dry DMF was stirred in an ice-bath for 30 minutes. Next, 10.7 mL (75 mmol) of 1-(2-aminoethyl)piperidine (Aldrich, Milwaukee, Wis.) was added, and the resulting solution was warmed to 25° C. and stirred 60 minutes. The mixture was poured into 200 mL ethyl acetate, and washed sequentially with 200 mL each of 2.5% aqueous HCl solution, brine, saturated aqueous sodium bicarbonate solution, and finally twice with brine. The mixture was then dried over anhydrous sodium sulfate and concentrated at reduced pressure to give 33.7 g (94%) of (S)-[2-(4-benzyloxy-phenyl)-1-(2-piperidin-1-yl-ethylcarbamoyl)-ethyl]-carbamic acid tert-butyl ester as a pale amber solid; mp 54–61° C.

APCI-MS: m/z 482.0 (MH$^+$).

Step B (S)-2-Amino-3-(4-benzyloxy-phenyl)-N-(2-piperidin-1-yl-ethyl)-propionamide

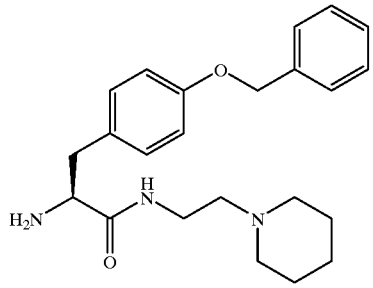

A solution of 33.7 g (70 mmol) 3-(4-benzyloxy-phenyl)-2-tert-butoxycarbonylamino-]-N-(2-piperidin-1-yl-ethyl)-propionamide in 150 mL dichloromethane was treated with 14 mL 2,2,2-triflouroacetic acid and the resulting solution was stirred for 3 hours at 25° C. The mixture was concentrated at reduced pressure to a viscous amber oil to which was added 300 mL saturated aqueous sodium bicarbonate solution. The resulting mixture was extracted with two 150 mL portions of ethyl acetate. The combined extracts were washed with 200 mL portions of saturated aqueous sodium bicarbonate solution and brine, dried over anhydrous sodium sulfate and concentrated at reduced pressure affording 22.6 g (85%) of (S)-2-Amino-3-(4-benzyloxy-phenyl)-N-(2-piperidin-1-yl-ethyl)-propionamide; mp 58–61 ° C.

APCI-MS: m/z 382.2.

Step C

A mixture of 1.67 mL (10 mmol) 4-(t-butyl) benzaldehyde, and 3.81 g (10 mmol) 3-(4-benzyloxy-phenyl)-2-amino-]-N-(2-piperidin-1-yl-ethyl)-propionamide in 65 mL dichloromethane was stirred at 25° C. for 30 minutes, cooled to 3° C. and treated with 3.18 g (15 mmol) sodium triacetoxyborohydride. After stirring 30 minutes at 3° C., the mixture was warmed to 25° C. and stirred for 60 hours, at which time 100 mL saturated aqueous sodium bicarbonate solution was added. The layers were separated, and the aqueous layer was extracted with two 40 mL portions of dichloromethane. The combined extracts were dried over anhydrous magnesium sulphate and concentrated at reduced pressure. The residue thus obtained was purified by column chromatography using 1:1 ethyl acetate-:hexane as eluant. There was obtained 1.314 g (19%) of the title compound dihydrate as a pale yellow foam.

APCI-MS: m/z 674.2 (MH$^+$).

Microanalysis for $C_{45}H_{50}N_3O_2 \cdot 2H_2O$:

Calculated: C, 76.10; H, 8.94; N, 5.92; $H_2O$, 5.07.

Found: C, 76.27; H, 9.01; N, 5.89; $H_2O$, 5.20.

EXAMPLE 11

3-(4-Benzyloxy-phenyl)-$N^2$,$N^2$-bis-(4-tert-butyl-benzyl)-$N^1$-(2-piperidin-1-yl-ethyl)-propane-1,2-diamine

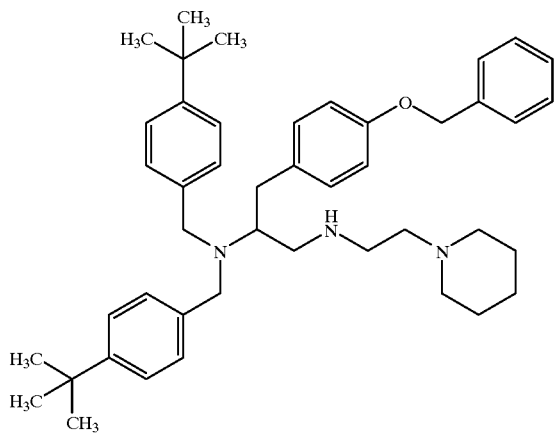

A solution of 900 mg (1.75 mmol) 3-(4-benzyloxy-phenyl)-2-[bis-(4-tert-butyl-benzyl)-amino]-N-(2-piperidin-1-yl-ethyl)-propionamide (Example 10) in 36 mL dry THF was treated portionwise with 332 mg (8.76 mmol) lithium tetrahydriodoaluminate, and the resulting suspension was heated under reflux for 16 hours. The mixture was then carefully quenched with 0.4 mL $H_2O$, followed by 2.0 mL 2 N NaOH solution, and finally 0.8 mL $H_2O$. The mixture was filtered and the solids washed with chloroform. The filtrate was treated with 50 mL $H_2O$, and after layers separated, the aqueous layer was extracted with an additional 50 mL chloroform. The combined organic extracts were washed with brine, dried over anhydrous magnesium sulphate, and concentrated at reduced pressure to give 832 mg of an amber oil. The oil was purified by column chromatography on silica gel (230–400 mesh) using 2% to 5% methanol in chloroform as eluant to give 612 mg (69%) of the title compound as a viscous, pale yellow liquid.

APCI-MS: m/z 660.2 ($MH^+$).

Microanalysis for $C_{45}H_{61}N_3O$:

Calculated: C, 81.89; H, 9.32; N, 6.37.

Found: C, 81.54; H, 9.21; N, 6.22.

EXAMPLE 12

3-(4-Benzyloxy-phenyl)-$N^2$-(4-tert-butyl-benzyl)-$N^1$-(2-piperidin-1-yl-ethyl)-propane-1,2-diamine

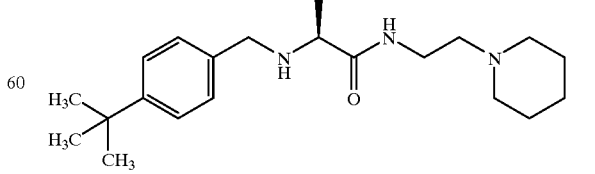

A solution of 700 mg (1.36 mmol) 3-(4-benzyloxy-phenyl)-2-(4-tert-butyl-benzylamino)-N-(2-piperidin-1-yl-ethyl)-propionamide (Example 13) in 28 mL dry THF was treated portionwise with 258 mg (6.80 mmol) lithium tetrahydriodoaluminate, and the resulting suspension was heated under reflux for 24 hours. The mixture was then carefully quenched with 0.35 mL $H_2O$ and filtered, and the resulting solids were washed with THF. The filtrate was diluted with 30 mL $H_2O$, and the THF removed under reduced pressure. The aqueous layer was extracted with three 40 mL portions of ethyl acetate. The combined organic extracts were washed with 100 mL each of saturated aqueous sodium bicarbonate solution and brine, dried over anhydrous magnesium sulphate, and concentrated at reduced pressure to give an amber oil. The oil was purified by column chromatography on silica gel (230–400 mesh) using 20% methanol in chloroform as eluant to give 141 mg (20%) of the title compound as a viscous, pale yellow liquid.

Microanalysis for $C_{34}H_{47}N_3O.0.25H_2O$:

Calculated: C, 78.80; H, 9.24; N, 8.11.

Found: C, 78.64; H, 9.56; N, 7.95.

TLC: Silica gel, $R_f$ 0.21 (25% $MeOH/CHCl_3$).

EXAMPLE 13

(S)-3-(4-Benzyloxy-phenyl)-2-(4-tert-butyl-benzylamino)-N-(2-piperidin-1-yl-ethyl)-propionamide A mixture of 0.5 mL (3 mmol) 4-(t-butyl)-benzaldehyde, and 5.72 g (15 mmol) (S)-3-(4-benzyloxy-phenyl)-2- amino-]-N-(2-piperidin-1-yl-ethyl)-propionamide (Example 10, Step B) in 30 mL dichloromethane was cooled to 3° C., stirred for 40 minutes, then treated with 953 mg (4.5 mmol) sodium triacetoxyborohydride. After stirring 30 minutes at 3° C., the mixture was warmed to 25° C. and stirred for 60 hours, then poured into 50 mL saturated aqueous sodium bicarbonate solution and stirred for 30 minutes. The layers were separated, and the aqueous layer was extracted with two 25 mL portions of dichloromethane, which were combined and dried over anhydrous magnesium sulphate, and concentrated at reduced pressure. The oily residue thus obtained was purified by column chromatography using 10% to 15% methanol in chloroform as eluant. There was obtained 2.12 g of an amber oil which was further purified by column chromatography using 10% methanol in chloroform as eluant affording 1.16 g (14%) of the title compound dihydrate as a pale yellow solid.

APCI MS m/z 528.4 [MH$^+$].

Microanalysis for $C_{34}H_{45}N_3O_2 \cdot 0.5$ MeOH:

Calculated: C, 76.20; H, 8.71; N, 7.73.

Found: C, 76.33; H, 8.63; N, 7.87.

EXAMPLE 14

3-(-4-Benzyloxy-phenyl)-N$^1$-tert-butyl-N$^2$-(4-tert-butyl-benzyl)-propane-1,2-diamine

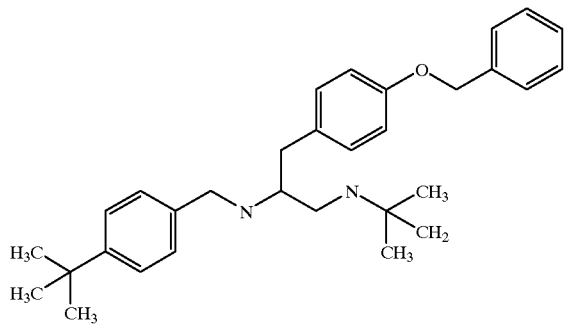

Step A

N-[2-(4-Benzyloxy-phenyl)-1-tert-butylcarbamoyl-ethyl]-4-tert-butyl-benzamide

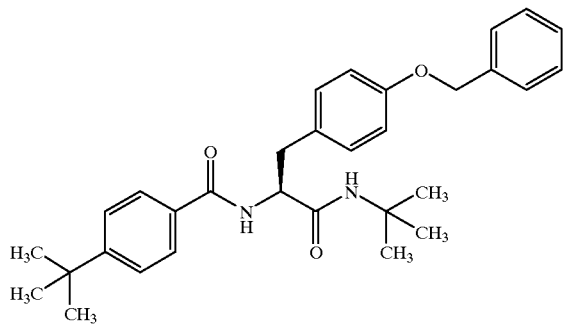

A solution of 0.589 g (3.026 mmol) 4-tert-butylbenzoic acid (Aldrich, Milwaukee Wis.) 1.06 mL (6.5 mmol) N,N-diisopropylethylamine, and 1.15 g (3.026 mmol) O-Benzotriazol-1-yl-N,N,N',N'-bis(tetramethylene)-uronium hexafluorophosphate in 6 mL dry DMF was stirred in an ice bath for 35 minutes, when 1.00 g (3.026 mmol) of 2-Amino-3-(4-benzyloxy-phenyl)-N-tert-butyl-propionamide (Example 1, Step B) was added. The resulting solution was warmed to 25° C. and stirred for 60 minutes. The mixture was poured into 20 mL diethyl and washed sequentially with 25 mL each of saturated aqueous sodium bicarbonate solution and twice with brine. The mixture was then dried over anhydrous sodium sulfate and concentrated at reduced pressure giving a pale amber solid that was purified by column chromatography on silica gel with 30% ethyl acetate in hexane to give N-[2-(4-benzyloxy-phenyl)-1-tert-butylcarbamoyl-ethyl]-4-tert-butyl-benzamide as a white solid; mp 124–131° C.

APCI-MS: m/z 487.4 [MH$^+$].

Step B

A solution of 126 mg (0.26 mmol) N-[2-(4-benzyloxy-phenyl)-1-tert-butylcarbamoyl-ethyl]-4-tert-butyl-benzamide in 1 mL dry THF was treated via dropwise addition with 0.78 mL (0.78 mmol) of a 1.0 M solution of borane-THF complex in THF. The resulting solution was heated under reflux for 8 hours. The mixture was cooled to 25° C. and 1 mL of 5 M HCL solution was carefully added, dropwise, followed by neutralization with saturated aqueous sodium bicarbonate. The mixture was extracted with three 7 mL portions of ethyl acetate. The combined extracts were washed with two 25 mL portions brine, dried over anhydrous magnesium sulfate and concentrated to a hazy oil. The oil was purified by column chromatography on silica gel with 5:5:1 ethyl acetate: hexanes:methanol as eluant. There was obtained 58 mg (49%) of a clear, colorless oil that slowly crystallized to white, waxy crystals of title product; mp 63–65° C.

APCI-MS: m/z 459.4 [MH$^+$].

EXAMPLE 15

Biological Activity

The compounds of the present invention exhibit valuable biological properties because of their ability to block calcium flux through N-type voltage-gated calcium channels. In addition to their ability to block N-type $Ca^{2+}$ channels, the compounds of the present invention were also evaluated for their ability to inhibit calcium flux through L-type $Ca^{2+}$ channels and Na and K channels in superior cervical ganglia (SCG) neurons. To measure interaction at the N-type $Ca^{2+}$ channel and calcium flux inhibition, the effects of the compounds of the present invention were measured in the assays described below.

Measurement of N-type $Ca^{2+}$ Channel Blocking Potencies of Compounds in IMR-32 Cells Using the Fluorescent $Ca^{2+}$ Indicator Indo-1

IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 $\mu$M nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

Methods

The IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimicotic mixture (Gibco). At approximately 80% confluency, differentiation was induced by the addition of 1 mM dibutyryl cAMP and 2.5 $\mu$M bromodeoxyuridine to the medium. After 7 to 13 days of differentiation, cells were detached using 0.5 mM EDTA and loaded with 5

μM Indo-1 acetoxymethyl ester (Molecular Probes, Eugene, Oreg.) at 300° C. for 45 minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostated cuvette holder with stirring capabilities, as well as with a computer-controlled pump that allowed for reagent addition during measurement. Instrument control and data collection was done by PTI's OSCAR software running on an IBM compatible computer. Different concentrations of the test compounds (60 μL in dimethyl sulfoxide) were added to 5.94 mL of assay buffer containing approximately $3\times10^6$ loaded cells, and 5 μM Nitrendipine (in 30 μL EtOH) to block L-type $Ca^{2+}$ channels. Samples were incubated for 10 minutes at 30° C. and then aliquoted into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 μL of stimulation solution (1 M KCl, 68 mM $CaCl_2$) to the cuvette via the computer-controlled pump. Ratio of dual emission signals (400 nm/490 nm), which is proportional to intracellular $Ca^{2+}$ concentration, was plotted against time, and the difference between maximal response after stimulation and basal value before stimulation) was determined. Values obtained in this way were plotted as a function of drug concentration. $IC_{50}$ values of test compounds were calculated by fitting a four-parameter logistic function to the data using the least method. The results are presented in Table 1.

stimulation was approximately 100 dB at the floor of the chamber. Mice were placed within the chamber and allowed to acclimatize for 1 minute. DBA/2mice in the vehicle-treated group responded to the sound stimulus (applied until tonic extension occurred, or for a maximum of 60 seconds) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds.

The incidence of all the seizure phases in the drug-treated and vehicle-treated mice was recorded, and the occurrence of tonic seizures were used for calculating anticonvulsant $ED_{50}$ values by probit analysis. Mice were used only once for testing at each time and dose point. Results of this assay are shown below in Table 2.

TABLE 2

| Example Number | Dose (mg/kg, IV) | Time Post Treatment (minutes) | Number of Mice Protected from Tonic Convulsions* |
|---|---|---|---|
| 3 | 30 | 15 | 4/5 |
| 6 | 30 | 15 | 2/5 |
| 6 | 30 | 45 | 4/5 |
| 12 | 10 | 15 | 0/5 |
| 13 | 30 | 15 | 4/5 |
| 13 | 30 | 45 | 4/5 |
| 13 | 10 | 15 | 0/5 |
| 13 | 10 | 45 | 1/5 |
| 14 | 30 | 15 | 5/5 |
| 14 | 30 | 45 | 4/5 |

*Number of mice protected from tonic convulsions/Number of mice tested

TABLE 1

| Cmpd of Example No. | IMR32 $IC_{50}$ (μM) | Cmpd of Example No. | IMR32 $IC_{50}$ (μM) | Cmpd of Example No. | IMR32 $IC_{50}$ (μM) | Cmpd of Example No. | IMR32 $IC_{50}$ (μM) |
|---|---|---|---|---|---|---|---|
| 1 | 1.2 | 5 | 27%@1 61%@10 | 9 | 2 | 13 | 0.7 |
| 2 | 2 | 6 | 0.44 | 10 | 0.68 | 14 | 0.45 |
| 3 | 0.76 | 7 | 1.4 | 11 | 0.17 | | |
| 4 | 45%@1 102%@10 | 8 | 0.79 | 12 | 0.28 | | |

Audiogenic Seizure Model in DBA/2 Mice
In Vivo Biological Protocol

A compound of the present invention was dissolved in water using 10% (weight/volume) Emulphor (GAF Corp., Wayne, N.J.) surfactant. Substances were administered by intravenous injection into the retro-orbital venous sinus. All testing was performed 15 minutes or 45 minutes after drug injection. All the male mice, 3 to 4 weeks old, were obtained from Jackson Laboratories, Bar Harbour, Me. Immediately before anticonvulsant testing, mice were placed upon a wire mesh, 4 inches square suspended from a steel rod. The square was slowly inverted through 180 degrees, and the mice were observed for 30 seconds. Any mouse falling from the wire mesh was scored as ataxic.

Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during

What is claimed is:
1. A compound having structural formula:

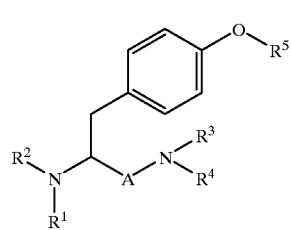

I and pharmaceutically acceptable salts and esters thereof, wherein $R^1$ and $R^2$ are independently H, phenylcyclopentylcarbonyl, $C_1$–$C_7$ alkyl, cyclohexylmethyl, benzyl, $C_1$–$C_5$ alkylbenzyl, or $C_1$–$C_5$ alkoxybenzyl;

A is —C(O)— or —CH$_2$—;

R$^3$ is H or —CH$_3$;

R$^4$ is C$_1$–C$_4$ alkyl;

R$^5$ is phenyl-(CH$_2$)$_n$—, C$_1$–C$_4$ alkylphenyl-(CH$_2$)$_n$—, or halophenyl-(CH$_2$)$_n$—; and n is 1 or 2.

2. The compound according to claim 1 selected from the group consisting of:

(S)-1-Phenyl-cyclopentanecarboxylic acid [2-(4-benzyloxy-phenyl)-1-tert-butylcar-bamoyl-ethyl]-amide;

(S)-3-(4-Benzyloxy-phenyl)-N-tert-butyl-2-(3-methyl-butylamino)-propionamide;

(S)-3-(4-Benzyloxy-phenyl)-2-[bis-(3-methyl-butyl)-amino]-N-tert-butyl-propion-amide;

(S)-3-(4-Benzyloxy-phenyl)-N-tert-butyl-2-[4-methyl-1-(3-methyl-butyl)-pentyl-amino]-propionamide;

(S)-3-(4-Benzyloxy-phenyl)-N-tert-butyl-2-[-cyclohexyl-methyl-(3-methyl-butyl)-amino]-propionamide;

(S)-3-(4-Benzyloxy-phenyl)-N-tert-butyl-2-[(3,3-dimethyl-butyl)-(3-methyl-butyl)-amino]-propionamide;

(S)-3-(4-Benzyloxy-phenyl)-N-tert-butyl-2-(3,3-dimethyl-butylamino)-propionamide;

(S)-3-(4-Benzyloxy-phenyl)-2-[bis-(3,3-dimethyl-butyl)-amino]-N-tert-butyl-propion-amide;

(S)-3-(4-Benzyloxy-phenyl)-N-tert-butyl-2-(4-tert-butyl-benzylamino)-propionamide; and 3-(4-Benzyloxy-phenyl)-N$^1$-tert-butyl-N$^2$-(4-tert-butyl-benzyl)-propane-1,2-diamine.

3. A therapeutic composition comprising an effective amount of the compound of claim 1 with a pharmaceutically acceptable carrier.

4. A therapeutic composition comprising an effective amount of the compound of claim 2 with a pharmaceutically acceptable carrier.

5. A method of blocking calcium channels, the method comprising administering to a mammal in need of calcium channel blocking a therapeutically effective amount of a compound of claim 1.

6. A method of blocking calcium channels, the method comprising administering to a mammal in need of calcium channel blocking a therapeutically effective amount of a compound of claim 2.

7. A method of treating stroke, the method comprising administering to a mammal having a stroke a therapeutically effective amount of a compound of claim 1.

8. A method of treating stroke, the method comprising administering to a mammal having a stroke a therapeutically effective amount of a compound of claim 2.

9. A method of preventing a stroke, the method comprising administering to a mammal at risk of having a stroke a therapeutically effective amount of a compound of claim 1.

10. A method of preventing a stroke, the method comprising administering to a mammal at risk of having a stroke a therapeutically effective amount of a compound of claim 2.

11. A method of treating cerebral ischemia, the method comprising administering to a mammal having cerebral ischemia a therapeutically effective amount of a compound of claim 1.

12. A method of treating cerebral ischemia, the method comprising administering to a mammal having cerebral ischemia a therapeutically effective amount of a compound of claim 2.

13. A method of treating head trauma, the method comprising administering to a mammal having head trauma a therapeutically effective amount of a compound of claim 1.

14. A method of treating head trauma, the method comprising administering to a mammal having head trauma a therapeutically effective amount of a compound of claim 2.

15. A method of treating pain, the method comprising administering to a mammal having pain a therapeutically effective amount of a compound of claim 1.

16. A method of treating pain, the method comprising administering to a mammal having pain a therapeutically effective amount of a compound of claim 2.

17. A method of inhibiting N-type calcium channels in a cell, comprising contacting a cell having one or more N-type calcium channels with a compound of claim 1.

18. A method of inhibiting N-type calcium channels in a cell, comprising contacting a cell having one or more N-type calcium channels with a compound of claim 2.

* * * * *